(12) United States Patent
Adachi et al.

(10) Patent No.: US 8,691,505 B2
(45) Date of Patent: Apr. 8, 2014

(54) PROMOTER FOR USE IN TRANSFORMATION OF ALGAE

(75) Inventors: Masao Adachi, Kochi (JP); Takuma Okami, Kochi (JP); Keizo Nagasaki, Hatsukaichi (JP); Yuji Tomaru, Hatsukaichi (JP)

(73) Assignee: Kochi University, Kochi-Shi, Kochi (JP)

( * ) Notice: Subject to any disclaimer, the term of this patent is extended or adjusted under 35 U.S.C. 154(b) by 0 days.

(21) Appl. No.: 13/576,711

(22) PCT Filed: Feb. 10, 2011

(86) PCT No.: PCT/JP2011/052924
§ 371 (c)(1),
(2), (4) Date: Aug. 2, 2012

(87) PCT Pub. No.: WO2011/102301
PCT Pub. Date: Aug. 25, 2011

(65) Prior Publication Data
US 2013/0130389 A1 May 23, 2013

(30) Foreign Application Priority Data
Feb. 17, 2010 (JP) .................................. 2010-032633

(51) Int. Cl.
*C12Q 1/68* (2006.01)

(52) U.S. Cl.
USPC ........ 435/6.1; 435/6.11; 435/69.1; 435/320.1; 435/440; 536/23.1; 536/23.2; 536/23.4; 536/23.72; 536/24.1; 536/24.3

(58) Field of Classification Search
USPC ...................... 435/6.1, 320.1, 6.11, 69.1, 440; 536/22.1, 23.1, 23.2, 23.4, 23.72, 24.1, 536/24.3
See application file for complete search history.

(56) References Cited

FOREIGN PATENT DOCUMENTS

| CN | 85 1 01291 A | 4/1987 |
|---|---|---|
| CN | 1057859 A | 1/1992 |
| CN | 1063506 A | 8/1992 |
| WO | 2010/084969 A1 | 7/2010 |

OTHER PUBLICATIONS

Dunahay et al., "Genetic Transformation of the Diatoms Cyclotella Cryptica and *Navicula* Saprophila", Journal of Phycology, 1995, vol. 31, pp. 1004-1012.
Sakaue et al., "Development of gene expression system in a marine diatom using viral promoters of a wide variety of origin", Physiologia Plantarum, 2008, vol. 133, pp. 58-67.
Lohuis et al., "Genetic transformation of dinoflagellates (*Amphidinium* and *Symbiodinium*): expression of GUS in microalgae using heterologous promoter constructs", The Plant Journal, 1998, vol. 13, No. 3, pp. 427-435.
Walker et al., "Algal Transgenics in the Genomic Era", Journal of Phycology, 2005, vol. 41, pp. 1077-1093.
Tomaru et al., "Isolation and characterization of a new single-stranded DNA virus infecting the cosmopolitan marine diatom *Chaetoceros debilis* ", Aquatic Microbial Ecology, 2008, vol. 50, pp. 103-112.
Sambrook et al., "Molecular Cloning a Laboratory Manual", 2001, vol. 1, pp. 5.14-5.17.
Poulsen et al., "Molecular Genetic Manipulation of the Diatom *Thalassiosira pseudonana* (Bacillariophyceae)", Journal of Phycology, 2006, vol. 42, pp. 1059-1065.
Javahery et al., "DNA Sequence Requirements for Transcriptional Initiator Activity in Mammalian Cells", Molecular and Cellular Biology, Jan. 1994, vol. 14, No. 1, pp. 116-127.
McLeod et al., "Core Promoter Structure in the Oomycete *Phytophthora infestans*", Eukaryotic Cell, Feb. 2004, vol. 3, No. 1, pp. 91-99.
Purnell et al., "TFIID sequence recognition of the initiator and sequences farther downstream in *Drosophila* class II genes", Genes & Development, 1994, vol. 8, pp. 830-842.
Liston et al., "Analysis of a Ubiquitous Promoter Element in a Primitive Eukaryote: Early Evolution of the Initiator Element", Molecular and Cellular Biology, Mar. 1999, vol. 19, No. 3, pp. 2380-2388.
Miyagawa et al., "So-rui Kansensei Visus Promoter o Mochiita Kaisan Keiso no Keishitsu Tenkan-kei no Kaihatsu", Japanese Society for Marine Biotechnology Taikai Koen Yoshishu, 2009, vol. 12, p. 104[2-3P-8].
Tomaru et al., "Kaisan Fuyu Keiso *Chaetoceros lorenzianus* ni Kansen suru Shinki Kanjo Single Stranded DNA Virus ClorDNAV no Seijo", The Japanese Society of Fisheries Science Shuki Taikai Koen Yoshishu, 2009, p. 61[433].
Miyagawa et al., "Kaisan Keiso *Phaeodactylum tricornutum* no Ishu Yurai Promoter ni yoru Keishitsu Tenkan", Japanese Society for Marine Biotechnology Taikai Koen Yoshishu, 2007, vol. 10, p. 76[B-13].
Miyagawa et al., "Keiso Chaetoceros sp. no Keishitsu Tenkan-kei no Kakuritsu", The Japanese Society of Fisheries Science Shuki Taikai Koen Yoshishu, 2007, p. 139[1017].
Okami et al., "So-rui Virus Yurai Promoter o Mochiita Kaisan Keiso no Keishitsu Tenkan-kei no Kaihatsu", The Japanese Society of Fisheries Science Shuki Taikai Koen Yoshishu, Sep. 22, 2010, p. 68[541].
International Search Report in corresponding PCT Application No. PCT/JP2011/052924, dated Apr. 19, 2011.

(Continued)

*Primary Examiner* — Ardin Marschel
(74) *Attorney, Agent, or Firm* — Bacon & Thomas, PLLC (57) ABSTRACT

The problem to be solved by the present invention is to provide a highly-efficient transformation technology, specifically, a highly-efficient promoter used for transforming algae, a vector comprising the promoter, and a method for transforming algae by using the vector. The promoter according to the present invention is characterized in comprising a polynucleotide constituting a non-coding region located upstream of a gene encoding a structural protein of a ClorDNA virus, and the like.

16 Claims, 3 Drawing Sheets

(56) References Cited

OTHER PUBLICATIONS

Chinese Office Action in corresponding Application No. 201180008922.1, issued Mar. 21, 2013, English translation thereof.

Search Report dated Jul. 3, 2013 issued in corresponding European application No. 11 74 4588.

Tomaru et al. "Isolation and Characterization of a Single-Stranded RNA Virus Infecting the Bloom-Forming Diatom *Chaetoceros socialis*" Applied and Enviromental Microbiology, Apr. 2009, pp. 2375-2381 (Published online: Aug. 29, 2008).

Li et al. "The Integrative Expression of GUS Gene Driven by FCP Promoter in the Seaweed *Laminaria japonica* (Phaeophyta)" J. Appl. Phycol (2009) 21:287-293.

International Preliminary Examiner Report in corresponding International Application No. PCT/JP2011/052924 with English translation, (2011).

Reply in corresponding International Application No. PCT/JP2011/052924 with English translation, (2011).

English translation of Miyagawa et al., "So-rui Kansensei Visus Promoter o Mochiita Kaisan Keiso no Keishitsu Tenkan-kei no Kaihatsu", Japanese Society for Marine Biotechnology Taikai Koen Yoshishu, 2009, vol. 12, p. 104[2-3P-8].

English translation of Miyagawa et al., "Kaisan Keiso *Phaeodactylum tricornutum* no Ishu Yurai Promoter ni yoru Keishitsu Tenkan", Japanese Society for Marine Biotechnology Taikai Koen Yoshishu, 2007, vol. 10, p. 76[B-13].

English translation of Miyagawa et al., "Keiso *Chaetoceros* sp. no Keishitsu Tenkan-kei no. Kakuritsu", The Japanese Society of Fisheries Science Shuki Taikai Koen Yoshishu, 2007, p. 139[1017].

English translation of Tomaru et al., "Kaisan Fuyu Keiso *Chaetoceros lorenzianus* ni Kansen suru Shinki Kanjo Single Stranded DNA Virus ClorDNAV no Seijo", The Japanese Society of Fisheries Science Shuki Taikai Koen Yoshishu, 2009, p. 61[433].

English translation of Okami et al., "So-rui Virus Yurai Promoter o Mochiita Kaisan Keiso no Keishitsu Tenkan-kei no Kaihatsu", The Japanese Society of Fisheries Science Shuki Taikai Koen Yoshishu, Sep. 22, 2010, p. 68 [541].

Chinese Office Action in corresponding Chinese Application No. 201180008922.1, dated Oct. 15, 2013, with English translation.

SEQUENCE LISTING

<160> NUMBER OF SEQ ID NOS: 13

<210> SEQ ID NO 1
<211> LENGTH: 473
<212> TYPE: DNA
<213> ORGANISM: ClorDNA Virus

<400> SEQUENCE: 1

```
ggaacatcct ttgtgttcgt gatgcatttt tgcattgggg ttggttacca cccccatact      60
tgttgagacc aaaaaatcgc gttagtatca gaatcttacg ttggtataat ggacatgttg     120
tattgaccac gagcgcctgc cgtaggacgc cgcctgccag ggcaatactc gcctgccaaa     180
acagaaagaa agcgcgctac cagcgcaaga tgataggccc tcaggccgca ttatgggatg     240
ggggctgtat tggttaataa caggcgggac tcaacatgtc acactataaa atggacgaaa     300
aggattaagt taatattatt cctttcgtc cattttacgt aggattctac gtatctctgg      360
tatatcaaaa actgtacagt ttttagaaca gtacagtttt gaaaaaaact gtacaaaatg     420
ttgacacttg ctgtcaactc gtgacacgta ctcgtgtcat aaaataagtt ctt            473
```

<210> SEQ ID NO 2
<211> LENGTH: 49
<212> TYPE: DNA
<213> ORGANISM: Artificial Sequence
<220> FEATURE:
<223> OTHER INFORMATION: primer

<400> SEQUENCE: 2

```
ggggacaagt ttgtacaaaa aagcaggctt aggaacatcc tttgtgttc                  49
```

<210> SEQ ID NO 3
<211> LENGTH: 48
<212> TYPE: DNA
<213> ORGANISM: Artificial Sequence
<220> FEATURE:
<223> OTHER INFORMATION: primer

<400> SEQUENCE: 3

```
ggggacaact ttgtatagaa aagttgggtg aagaacttat tttatgac          48
```

<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4

```
gtaaaacgac ggccagt                                            17
```

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5

```
tccttttcgt ccatttttacg                                        20
```

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6

```
cagggcatgc tcatgtagag                                         20
```

<210> SEQ ID NO 7
<211> LENGTH: 510
<212> TYPE: DNA
<213> ORGANISM: ClorDNA Virus

<400> SEQUENCE: 7

```
ggttaattgg aacatccttt gtgttcgtga tgcattttg cattggggtt ggttaccacc    60
cccatacttg tttgagacca aaaaatcgcg ttagtatcag aatcttacgt tggtataatg  120
gacatgttgt attgaccacg agcgcctgcc gtaggacgcc gcctgccagg gcaatactcg  180
cctgccaaaa cagaaagaaa gcgcgctacc agcgcaagat gataggccct caggccgcat  240
tatgggatgg gggctgtatt ggttaataac aggcgggact caacatgtca cactataaaa  300
tggacgaaaa ggattaagtt aatattattc cttttcgtcc attttacgta ggattctacg  360
tatctctggt atatcaaaaa ctgtacagtt tttagaacag tacagttttg aaaaaaactg  420
tacaaaatgt tgacacttgc tgtcaactcg tgacacgtac tcgtgtcata aaataagttc  480
ttgtgtatta gaactgtatt gcaaggtatg                                  510
```

<210> SEQ ID NO 8
<211> LENGTH: 49
<212> TYPE: DNA
<213> ORGANISM: Artificial Sequence
<220> FEATURE:
<223> OTHER INFORMATION: primer

<400> SEQUENCE: 8

```
ggggacaagt ttgtacaaaa aagcaggctt acaacatgtc acactataa            49
```

<210> SEQ ID NO 9
<211> LENGTH: 49
<212> TYPE: DNA

<213> ORGANISM: Artificial Sequence
<220> FEATURE:
<223> OTHER INFORMATION: primer

<400> SEQUENCE: 9

```
ggggacaagt tgtacaaaaa aagcaggctt aaaaatgttg acacttgct                49
```

<210> SEQ ID NO 10
<211> LENGTH: 48
<212> TYPE: DNA
<213> ORGANISM: Artificial Sequence
<220> FEATURE:
<223> OTHER INFORMATION: primer

<400> SEQUENCE: 10

```
ggggacaact tgtatagaaa agttgggtg accttgcaat acagttct                  48
```

<210> SEQ ID NO 11
<211> LENGTH: 499
<212> TYPE: DNA
<213> ORGANISM: ClorDNA Virus

<400> SEQUENCE: 11

```
ggaacatcct ttgtgttcgt gatgcatttt tgcattgggg ttggttacca cccccatact    60
tgtttgagac caaaaaatcg cgttagtatc agaatcttac gttggtataa tggacatgtt   120
gtattgacca cgagcgcctg ccgtaggacg ccgcctgcca gggcaatact cgcctgccaa   180
aacagaaaga aagcgcgcta ccagcgcaag atgataggcc ctcaggccgc attatgggat   240
gggggctgta ttggttaata acaggcggga ctcaacatgt cacactataa aatggacgaa   300
aaggattaag ttaatattat tccttttcgt ccatttacg taggattcta cgtatctctg    360
gtatatcaaa aactgtacag ttttagaac agtacagttt tgaaaaaaac tgtacaaaat   420
gttgacactt gctgtcaact cgtgacacgt actcgtgtca taaataagt tcttgtgtat    480
tagaactgta ttgcaaggt                                                499
```

<210> SEQ ID NO 12
<211> LENGTH: 230
<212> TYPE: DNA
<213> ORGANISM: ClorDNA Virus

<400> SEQUENCE: 12

```
caacatgtca cactataaaa tggacgaaaa ggattaagtt aatattattc cttttcgtcc    60
atttttacgta ggattctacg tatctctggt atatcaaaaa ctgtacagtt tttagaacag  120
tacagttttg aaaaaaactg tacaaaatgt tgacacttgc tgtcaactcg tgacacgtac   180
tcgtgtcata aataagttc ttgtgtatta gaactgtatt gcaaggtatg                230
```

<210> SEQ ID NO 13
<211> LENGTH: 143
<212> TYPE: DNA
<213> ORGANISM: ClorDNA Virus

<400> SEQUENCE: 13

```
caacatgtca cactataaaa tggacgaaaa ggattaagtt aatattattc cttttcgtcc    60
atttttacgta ggattctacg tatctctggt atatcaaaaa ctgtacagtt tttagaacag  120
tacagttttg aaaaaaactg tac                                           143
```

PROMOTER FOR USE IN TRANSFORMATION OF ALGAE

TECHNICAL FIELD

The present invention relates to a novel promoter used for transforming algae, a vector containing the promoter, and a method for transforming algae using the vector.

BACKGROUND ART

It is very important for energy issues to utilize sunlight, which is a permanent and stable energy source. Photosynthesis by plants is an excellent system capable of transforming sunlight energy to chemical energy most efficiently, and absorbs and assimilates carbon dioxide and excess nutrient salts in the environment. In addition, oxygen is emitted. The development of a technology utilizing plants is therefore expected as a solution for energy issues.

Among plants, algae live in both of seawater and freshwater, which abundantly exist; and are therefore huge in amount. In addition, algae have significant photosynthesis ability. Further, some of algae produce a useful compound such as unsaturated fatty acid and anti-tumor compound. Furthermore, since some of diatoms produce a useful inorganic substance, a technology called as biomineralization by diatoms is focused. As described above, algae can be said to be important organisms as useful resources.

When an organism is utilized industrially, a transformation technology for introducing a useful gene is generally used. The transformation technology is also used for knocking out a specific gene or preventing the action thereof in order to elucidate the function of the gene.

The transformation of algae, especially diatoms and green algae, has been conventionally carried out. In such a conventional method, an endogenous promoter is isolated, a gene is conjugated with the promoter, and the promoter is introduced into algae. However, this method is far from efficient, since a lot of effort and time is required for isolating an endogenous promoter. There is also a problem that the transformation efficiency of algae, particularly of marine algae, is originally very low.

On the other hand, in transformation of animals or plants other than algae, a promoter derived from a virus rather than an endogenous promoter is generally used. For example, a CaMV35S promoter isolated from a cauliflower mosaic virus (CaMV) infecting cruciferous plants is used for transforming a wide range of plants without limited to cruciferous plants. For transformation of an animal cell, a CMV promoter isolated from a cytomegalovirus (CMV) and a SV40 promoter isolated from a simian virus 40 (SV40) are widely used.

Unlike the above situation, in transformation of algae, example in which an exogenous virus promoter is used is little known.

For example, Non-patent document 1 discloses an experimental example of transforming a diatom Cycrotela cryptica by using a CaMV35S promoter; however, it is reported that a transformant could not be obtained.

Non-patent document 2 discloses that a GUS (β-glucuronidase) gene was introduced into a diatom Phaeodactylum tricornutum by using a CMV promoter, a CaMV35S promoter or a Rous sarcoma virus (RSV) promoter; as a result, GUS was expressed in any cases.

Non-patent document 3 discloses that when a GUS gene is introduced into dinoflagellate Amphidinium or Symbiodinium by using a CaMV35S promoter, GUS was expressed. However, according to another document (Non-patent document 4), there is no report describing that transformation of dinoflagellates has been succeeded by other group in spite of diligent efforts.

PRIOR ART

Non-Patent Document

Non-patent document 1: Dunahay T. G. et al., Journal of Phycology, vol. 31, pp. 1004-1012 (1995)
Non-patent document 2: Sakaue K. et al., Physiologia plantarum, vol. 133, pp. 59-67 (2008)
Non-patent document 3: Lohuis M. R. et al., The Plant Journal, vol. 13, pp. 427-435 (1998)
Non-patent document 4: Walker T. L. et al., Journal of Phycology, vol. 41, pp. 1077-1093 (2005)

DISCLOSURE OF THE INVENTION

Problems to be Solved by the Invention

As described above, there are examples reporting success in transforming algae by using a viral promoter such as a CaMV35S promoter derived from a cauliflower mosaic virus, although the number of examples is very small.

However, there is also a report that transformant was not obtained or reproducibility was not achieved in such a condition. In general, since the transformation efficiency of algae, particularly marine algae, is very low, development of a transformation technology with high efficiency is much-needed.

Under the above-described situation, the problem to be solved by the present invention is to provide a highly-efficient transformation technology. In particular, the problem to be solved by the present invention is to provide a highly-efficient promoter used for transforming algae, a vector comprising the promoter, and a method for transforming algae by using the vector.

Means for Solving the Problems

The present inventors conducted intensive studies to solve the above-mentioned problem. As a result, the inventors found that a promoter located upstream of a gene considered as encoding a structural protein of a *Chaetoceros* cf. *lorenzianus* DNA virus (ClorDNA virus) is able to transform algae very efficiently, and accomplished the present invention.

The novel promoter according to the present invention is characterized in comprising any one of the following polynucleotide (1) to (3):

(1) a polynucleotide constituting a non-coding region located upstream of a gene encoding a structural protein of a ClorDNA virus;

(2) a polynucleotide corresponding to the polynucleotide (1) with one or more nucleotide deletions, substitutions or additions, and activating expression of a gene encoding an arbitrary protein in an algal cell;

(3) a polynucleotide hybridizing to a polynucleotide having a base sequence complementary to the sequence of the polynucleotide (1) in a stringent condition and activating expression of a gene encoding an arbitrary protein in an algal cell.

The vector according to the present invention is characterized in comprising the above promoter and a gene encoding an arbitrary protein.

The method for transforming an alga according to the present invention is characterized in comprising the steps of producing the above-described vector, and introducing the vector into the algal cell.

Effect of the Invention

By using a vector containing the promoter according to the present invention, algae can be transformed efficiently. Therefore, it becomes possible according to the present invention to efficiently transform algae, of which transformation is difficult and for which the transformation technology has not been adequately examined although algae exist abundantly and have excellent characteristics such as high photosynthetic capability and producibility of useful substance; as a result, useful material can be produced in large volume.

BRIEF DESCRIPTION OF THE DRAWINGS

FIG. 2(1) demonstrates a structure of a plasmid vector containing an fcp promoter of *T. pseudonana*; and FIG. 2(2) demonstrates a structure of a plasmid vector without promoter.

MODE FOR CARRYING OUT THE INVENTION

The first promoter according to the present invention has (1) a polynucleotide constituting a non-coding region located upstream of a gene encoding a structural protein of a ClorDNA virus.

A ClorDNA virus infects a diatom *Chaetoceros* cf. *lorenzianus*. There are conventionally few examples reporting a virus representing infectiousness on algae, particularly on marine algae; however, the present inventors have succeeded in isolating a variety of viruses from algae such as raphidophyceae, dinoflagellates and diatoms in recent years. The ClorDNA virus according to the present invention is one of the marine algae infectious viruses isolated by the present inventors.

The gene which encodes a structural protein is not particularly limited as far as the gene is involved in the expression of a structural protein of ClorDNA virus and actively expressed.

In the present invention, a coding region means a part that is translated into a protein through mRNA, and a non-coding region means a part other than the coding region. In other words, a non-coding region means a part located upstream of a start codon such as ATG, and includes not only a part that is not transcribed into mRNA but also a part that is not translated into a protein although it is transcribed into mRNA.

In general, a promoter has a core element that holds the key of transcription, and a regulatory element that promotes or prevents transcription. When a gene is introduced, it is particularly important to utilize a core element. As such a core element, a TATA box, an initiator element (Inr), a downstream element and the like are known; and as a regulatory element, a CAAT box, a GATA box and the like are known. The present inventors examined a nucleotide sequence in the region upstream of an ORF region of a ClorDNA virus; as a result, found 5'-CAAT-3' as a CAAT box I, 5'-TATAAA-3' as a TATA box, 5'-ACGTA-3' as a ACGTA box, and 5'-TCA$_{+1}$TAAA-3' as an initiator element (Inr) of algae. In addition, the present inventors demonstrated that a promoter containing the above-described Inr has no function in Centric diatoms. The promoter is derived from Cset DNA virus, which is one of the viruses related to ClorDNA virus according to the present invention. From the above-described findings, it is highly possible that since an unknown sequence other than the above-described initiator element functions as a core element, the polynucleotide (1) according to the present invention can display high transformation ability.

The polynucleotide (1) is exemplified by polynucleotides having base sequences of SEQ ID NO: 13, SEQ ID NO: 12, SEQ ID NO: 11 and SEQ ID NO: 1.

The second promoter according to the present invention is (2) a polynucleotide which corresponds to the polynucleotide (1) with one or more nucleotide deletions, substitutions or additions and which activates expression of a gene encoding an arbitrary protein in an algal cell.

In the polynucleotide (2), the number of nucleotides that are deleted, substituted or added is preferably not less than 1 and not more than 200, more preferably not less than 1 and not more than 100, further preferably not less than 1 and not more than 70, further preferably not less than 1 and not more than 30, further preferably not less than 1 and not more than 20, further preferably not less than 1 and not more than 10, and particularly preferably not less than 1 and not more than 5.

The third promoter of the present invention is (3) a polynucleotide which hybridizes to a polynucleotide having a base sequence complementary to the sequence of the polynucleotide (1) in a stringent condition and which activates expression of a gene encoding an arbitrary protein in an algal cell.

In terms of the polynucleotide (3), the stringent condition means that a nucleotide is hybridized at 65° C. in 2×SSC containing 0.1% SDS and then washed twice with 0.1×SSC-0.1% SDS.

In terms of the polynucleotides (2) and (3), the polynucleotide that activates expression of a gene encoding an arbitrary protein in an algal cell means a polynucleotide capable of allowing expression of a gene which encodes an arbitrary protein and is conjugated downstream of the polynucleotide, when the polynucleotide is introduced into the algal cell.

In terms of the polynucleotides (2) and (3), the homology with the polynucleotide (1) is preferably not less than 50%, more preferably not less than 70%, further preferably not less than 80%, further preferably not less than 90%, further preferably not less than 95%, further preferably not less than 98%, and particularly preferably not less than 99%.

The polynucleotides (1) to (3) can be isolated from the upstream sequence of a gene encoding a structural protein of a ClorDNA virus or a mutant thereof. However, the polynucleotides may be chemically synthesized. The polynucleotides (1) to (3) can be amplified from a template by PCR, to be used.

The vector according to the present invention includes the above promoter and a gene encoding an arbitrary protein.

The kind of the vector is not particularly limited as far as the vector can be introduced into an algal cell, and any of a plasmid vector and a virus vector may be used. Since it can be hardly said that researches of virus which infects algae, particularly marine algae, are sufficiently advanced, a plasmid vector is preferably used.

In the present invention, the "arbitrary protein" is not particularly limited, and may be any useful proteins which are desired to be produced.

The vector according to the present invention may include other sequences that are included in a general vector. As such sequences, a selection marker gene for identifying algae into which the vector of the present invention is introduced, and a terminator functioning in an algal cell can be exemplified.

As a method for preparing the vector according to the present invention, ordinary methods may be used. For example, each sequences described above and a donor vector may be digested with a restriction enzyme, annealed, and the annealed sequences may be bound using a DNA ligase. Alternatively, each sequences may be cloned into a vector by a simple known method utilizing a Clonase reaction.

The method for transforming an alga according to the present invention is characterized in comprising the steps of producing the above-described vector, and introducing the vector into the algal cell.

As a method for preparing the vector of the present invention, the methods known by a person skilled in the art may be used as described above.

As a method for introducing the vector of the present invention into an algal cell, known methods such as a particle gun method, a glass beads stirring method, a microinjection method, an agrobacterium method, a lithium acetate method, a calcium phosphate method and a protoplast method may be used. However, in the case of marine algae, an electroporation method is not appropriate since marine algae need to be grown in a media having high salt concentration.

The algal cell transformed with the vector of the present invention can be identified by being cultured in a selection medium suited for the introduced selection marker gene.

EXAMPLES

Hereinafter, the present invention is described in more detail by demonstrating Examples; however, the present invention is not limited by the Examples, and of course, may be practiced with appropriate modification within the range conforming to the above or below description, and any of the modifications are included within the technical scope of the present invention.

Example 1

Separation of a ClorDNA Virus Promoter According to the Present Invention (1) Extraction of Genomic DNA of a Virus Infecting Marine Algae According to the method described in Tomaru, Y. et al., Aquatic Microbial Ecology, vol. 50, pp. 103-112 (2008), a genome was extracted from a *Chaetoceros lorenzianus* DNA virus (ClorDNA virus) living on a centric diatom *Chaetoceros* cf. *lorenzianus* as a host.

Specifically, first, algal cell debris and the like were removed from a viral liquid (10 mL) by a filtration using a 0.22 μm filter (manufactured by MILLIPORE, Millex-GS, pore size: 0.22 μm). To the obtained filtrate, 40% polyethyleneglycol 6000 solution (manufactured by Wako) was added to make the final concentration to be 10 w/v %. The mixture was left still at 4° C. overnight. The mixture was then transferred into a centrifugal tube (manufactured by Nalgen, Ultra-Bottle Assemblies), and centrifuged at 57,000×g, 4° C. for 1.5 hours using an ultracentrifuge (manufactured by BECKMAN, Ultracentrifuge L8-70M). Then, the supernatant was removed. To the obtained precipitate, a phosphate buffer (10 mM sodium dihydrogen phosphate, 10 mM sodium hydrogen phosphate, pH 7.2, 5 mL) was mixed to wash viral particles.

Again, after the mixture was centrifuged at 217,000×g, 4° C. for 4 hours and the supernatant was removed in a similar manner, the obtained precipitate was dissolved in sterilized purified water (manufactured by Millipore, milliQ (registered trademark), 300 μL). The solution was transferred into a 1.5 mL Eppendorf tube, and proteinase K and 10% sarcosyl were added thereto to make the respective final concentrations to be 1 mg/mL and 1 w/v %. The mixture was incubated at 55° C. for 1.5 hours. Then, a phenol/chloroform treatment and a chloroform treatment were carried out with routine methods. To the obtained supernatant, a one-tenth amount of 3M sodium acetate (pH 4.8) was added, and further a 2.5 times amount of ethanol was added. The resultant solution was left still at −80° C. for 1 hour. Then, the solution was centrifuged at 14,000 rpm, 4° C. for 10 minutes using a high-speed micro centrifuge (manufactured by KUBOTA, KUBOTA3740), and the obtained precipitate was washed with 70% ethanol and then dried. The dried product was dissolved in sterilized milliQ water (20 μL) to obtain a DNA solution.

(2) Separation of ClorDNA Virus Promoter

The sequence information of the genomic DNA of the ClorDNA virus obtained in the above (1) was analyzed using ORF finder (NCBI) to search ORF: open reading frames contained therein; and then, the sequence information was compared with a database using Blast (DDBJ), to detect the ORF of structural protein. The sequence which was located upstream of the ORF region and which had 507 bases is shown as SEQ ID NO: 7. In SEQ ID NO: 7, the sequence "ATG" at 3' end is a start codon of the ORF. The region from $482^{nd}$ base which corresponded to $26^{th}$ base upstream from the ATG sequence which seemed to be a translation starting point in this sequence to $9^{th}$ base was amplified by PCR using a ClP2L/attB1 primer (SEQ ID NO: 2) and a ClP2/attB4 primer (SEQ ID NO: 3). The base sequence of from $5^{th}$ to $29^{th}$ in SEQ ID NO: 2 and the base sequence of from $5^{th}$ to $28^{th}$ in SEQ ID NO: 3 show attB sequences required for BP Clonase reaction for construction of a plasmid as described later. The base sequence of the obtained ClorDNA virus promoter is shown as SEQ ID NO: 1. In SEQ ID NO: 1, the $460^{th}$ base "T" is considered to be a transcription initiation point.

The conditions of the PCR are shown as follows. As a PCR mixture, a 5× buffer (manufactured by TaKaRa, 5 μL), dNTP Mix (manufactured by TaKaRa, 2 μL), Prime Star HS (manufactured by TaKaRa, 0.25 μL, 5 U/μL), genomic DNA of ClorDNA virus (1 μL) and two primers (10 pmol/μL, each 1 μL) were mixed, and lastly sterilized milliQ water was added to make the total volume to be 25 μL. Then, the cycle of 10 seconds at 98.0° C., 30 seconds at 40.0° C. and 60 seconds at 72.0° C. was repeated 30 times, followed by a final reaction at 72.0° C. for 5 minutes.

For confirming amplification of a fragment, electrophoresis was conducted. For the electrophoresis, a TAE buffer (Tris acetate buffer) and agarose S (manufactured by NIPPON GENE Co., Ltd.) 1.5% gel were used. A sample for electrophoresis was prepared by adding 1 μL of a 10× loading buffer (manufactured by TaKaRa) to each 9 μL of the PCR product to be mixed. As a DNA molecular weight marker, 100 bp ladder (manufactured by TOYOBO, Code No. DNA-030X, 2 μL) was used and electrophoresed concurrently. Electrophoresis was carried out in a condition of 100 V for about 30 minutes using a Mupid electrophoresis tank (manufactured by ADVANCE Co., Ltd.). After the electrophoresis, the gel was stained by a routine method (Sambrook and Russell, 2001) using ethidium bromide and photographed under ultraviolet irradiation.

Example 2

Preparation of Vector Containing ClorDNA Virus Promoter According to the Present Invention (1) Preparation of Each Entry Clone Plasmid An entry clone plasmid vector into which the ClorDNA virus promoter obtained in Example 1, a Nourseothricin resistance gene (nat) (Poulsen, N. et al., Journal of Phycology, 42, pp. 1059-1065 (2006)) as a transgene and an fcp terminator of *Thalassiosira pseudonana* (Poulsen, N. et al., Journal of Phycology, 42, pp. 1059-1065 (2006)) were introduced was prepared using Multisite Gateway (registered trademark) Pro Kit (manufactured by Invitrogen).

Specifically, a solution of the ClorDNA virus promoter which was obtained in Example 1 and which had an attB sequence required for the Clonase reaction for construction of a plasmid was purified using High pure PCR Cleanup Micro Kit (manufactured by Roche) in accordance with the instruction manual thereof. Then, the solution (50 fmoles) and a donor vector (manufactured by Invitrogen, pDONR221 P1-P4, 100 ng/µL) were mixed, and sterilized milliQ water was added to the solution to make a total amount to be 8 µL. The donor vector had an attP sequence required for a Clonase reaction for construction of a plasmid. To the mixture, BP Clonase (trade name) II Enzyme Mix (manufactured by Invitrogen, 2 µL) was further added to be mixed, and the mixture was allowed to react at 25° C. for 1 hour. To the reaction mixture, proteinase K (manufactured by Invitrogen, 1 µL) was then added. The mixture was treated at 37° C. for 10 minutes. The reaction mixture (2.5 µL) was mixed with One Shot (registered trademark) Mach 1 T1 (registered trademark) chemically competent cells (manufactured by Invitrogen, 25 µL), and the mixture was left still on ice for 30 minutes. Then, a heat shock treatment was carried out at 42° C. for 30 seconds, and the mixture was immediately transferred onto the ice and left still for 2 minutes. Next, SOC (manufactured by Invitrogen, 250 mL) was added thereto, and culture was carried out under shaking at 37° C. for 1.5 hours. The cultured bacterial mixture (275 µL) was spread on a LB agar medium (1% triptone, 0.5% yeast extract, 1% NaCl, 1.5% agar) containing 50 µg/mL kanamycin. The medium was cultured upside down in a multi shaker oven (manufactured by TAITECH) at 37° C. overnight (about 10 hours). The obtained colonies were inoculated to a LB liquid medium (10 mL) using a platinum loop, and cultured under shaking at 37° C. overnight. From the culture liquid (3 mL), an entry clone plasmid in which the ClorDNA virus promoter having an attP sequence required for LR Clonase reaction was introduced was extracted using Pure Yield Plasmid Miniprep System (manufactured by Promega).

Also, a Nourseothricin resistance gene (nat) having an attB sequence required for BP Clonase reaction for construction of a plasmid was amplified in a similar manner to Example 1, and introduced into pDONR221 P4r-P3r, which was a donor vector having an attP sequence required for BP Clonase reaction, in a similar manner as described above, to obtain an entry clone plasmid in which an antibiotic resistance gene having an attL sequence required for LR Clonase reaction was introduced.

Further, an fcp terminator of *Thalassiosira pseudonana* having an attB sequence required for BP Clonase reaction for construction of a plasmid was amplified in a similar manner to Example 1, and introduced into pDONR221 P3-P2, which was a donor vector having an attP sequence required for BP Clonase reaction, in a similar manner as described above, to obtain an entry clone plasmid into which a terminator having an attL sequence required for LR Clonase reaction was introduced.

(2) Preparation of Destination Plasmid

A destination plasmid was prepared by incorporating a Reading Frame Casette having an attR sequence required for LR Clonase reaction into a pBluescript SK– (manufactured by Stratagene) using Gateway Vector Conversion System with One Shot ccdB Survival (registered trademark) Competent Cells (manufactured by Invitrogen).

First, the pBluescript SK– (2 µg) was digested at 37° C. for 3 hours using 20 U of a restriction enzyme EcoRI (manufactured by TOYOBO, 10 U/µL). DNA was precipitated by adding ethanol to the reaction mixture according to a routine method, to be collected. Next, the DNA was blunted by using a T4 DNA polymerase. Specifically, to the collected DNA, a 10× buffer (5 µL), 2.5 mM dNTP (manufactured by TAKARA, 2 µL), T4 DNA polymerase (manufactured by TOYOBO, 0.5 U/µL, 1 µL) and sterilized milliQ water (42 µL) were added, to prepare a reaction mixture (50 µL in total). The reaction mixture was incubated at 12° C. for 15 minutes. To the reaction mixture, sterilized milliQ water (350 µL) was immediately added. The mixture was subjected to a phenol/chloroform treatment and a chloroform treatment according to routine methods, followed by ethanol precipitation to collect DNA. Next, for preventing recircularization of the plasmid digested with the restriction enzyme, the fragments were subjected to a 5'-end dephosphorylation treatment using CIAP (manufactured by TaKaRa, Calf intestine Alkaline Phosphatase). To the blant ended DNA, a 10×CIAP buffer (5 µL) and CIAP (0.1 U/µL, 1 µL) were added, and sterilized milliQ water was added to prepare a reaction mixture (50 µL in total). The reaction mixture was incubated at 37° C. for 15 minutes and sequentially at 56° C. for 15 minutes. Then, CIAP (0.1 U/µL, 1 µL) was added thereto again, and the mixture was incubated at 37° C. for 15 minutes and sequentially at 56° C. for 15 minutes. To the reaction mixture, a 10% SDS solution (2.5 µL), a 500 mM EDTA solution (0.5 µL) and a proteinase K solution (20 mg/µL, 0.5 µL) were further added, and the mixture was incubated at 56° C. for 30 minutes and sequentially at 75° C. for 10 minutes. Thereafter, a phenol/chloroform treatment and a chloroform treatment were carried out according to routine methods. Next, DNA was collected by ethanol precipitation, and dissolved in sterilized milliQ water (10 µL).

The obtained pBluescript SK– having blunt ends was mixed with a Reading Frame Casette A (manufactured by Invitrogen, RfA) for conjugation by using a T4 DNA ligase associated with pGEM-T Vector Systems Kit (manufactured by Promega). First, into a 0.2 mL PCR tube sterilized in an autoclave, a 2× rapid ligation buffer (manufactured by Promega, 5 µL), pBluescript SK– (100 ng/µL, 0.5 µL), RfA (5 ng/µL, 2 µL), T4 DNA ligase (manufactured by Promega, 3 U/µL, 1 µL) and sterilized milliQ water (1.5 µL) were added, to prepare a reaction mixture (10 µL in total). The reaction mixture was stored at room temperature for 1 hour, and incubated at 4° C. overnight (16 hours or more). This ligation solution (5 µL) was mixed with ccdB Survival Competent Cells (manufactured by Invitrogen, 50 µL), and the mixture was left still for 30 minutes on ice. Then, the mixture was subjected to a heat shock treatment at 42° C. for 30 seconds, immediately transferred onto ice, and left still for 2 minutes. Next, SOC (250 mL) was added thereto and the mixture was cultured under shaking at 37° C. for 1.5 hours. The cultured bacteria mixture (300 µL) was spread on a LB agar medium containing 25 µg/mL chloramphenicol and 50 µg/mL ampicillin. The medium was cultured upside down in a multi shaker oven at 37° C. overnight.

The obtained colonies were inoculated to a LB medium (10 mL) using a platinum loop, and cultured under shaking at 37° C. overnight. From the culture liquid (3 mL), a destination plasmid was extracted by using Pure Yield Plasmid Miniprep System (manufactured by Promega).

(3) Preparation of Expression Clone Plasmid Vector

An expression clone plasmid vector in which a promoter, an antibiotic resistance gene and a terminator were conjugated was prepared by conducting LR Clonase reaction between the entry clone plasmid obtained in Example 2(1) and the destination plasmid obtained in Example 2(2) using Multisite Gateway Pro Kit (manufactured by Invitrogen).

Specifically, three kinds of entry clone plasmids (each 10 fmoles) into which a promoter, an antibiotic resistance gene and a terminator were respectively incorporated were mixed with a destination vector (20 fmoles), and sterilized milliQ water was further added thereto to prepare a mixture (8 µL in total). To the mixture, LR Clonase II PLUS Enzyme Mix (manufactured by Invitrogen, 2 µL) was added to be mixed, and the mixture was allowed to react at 25° C. for 16 hours. Thereafter, proteinase K (manufactured by Invitrogen, 1 µL) was added to the reaction mixture, and the mixture was treated at 37° C. for 10 minutes. The reaction mixture (2.5 µL) was mixed with One Shot Mach 1 T1 (registered trademark) chemically competent cells (manufactured by Invitrogen, 25 µL), and the resultant mixture was left still on ice for 30 minutes. Then, the mixture was subjected to a heat shock treatment at 42° C. for 30 seconds, immediately transferred onto ice, and left still for 2 minutes. Next, SOC (250 µL) was added to the mixture and culture was carried out under shaking at 37° C. for 1.5 hours. The cultured bacteria mixture (275 µL) was spread on a LB agar medium containing 50 µg/mL ampicillin. The medium was cultured upside down in a multi shaker oven at 37° C. overnight. The obtained colonies were inoculated to a LB medium (200 mL) using a platinum loop, and cultured under shaking at 37° C. overnight. From the culture mixture, plasmid DNA was extracted using Nucleo-Bond (registered trademark) Xtra Midi (manufactured by MACHEREY-NAGEL) in accordance with the instruction manual thereof.

(4) Confirmation of DNA Sequence

For confirming that an intended expression clone plasmid vector was prepared, a nucleotide sequence was determined by using a Dideoxy method.

A cycle sequencing PCR was carried out by using the expression clone plasmid vector (200 ng) prepared in Example 2(3) as a template. The reaction condition is described as follows. The reaction mixture (10 µL) was composed of a template DNA (100 ng/µL, 2 µL), Big Dye Terminator Cycle Sequencing ver. 3.1 (manufactured by Applied Biosystems, 0.5 µL), a 5× sequencing buffer (2 µL), primer (1.6 µmol/µL, 0.66 µL) and sterilized distilled water (4.84 µL). As the primer, M13M3 primer (SEQ ID NO: 4) was used. As a reaction condition, after heating at 95° C. for 5 minutes, a cycle of at 96° C. for 10 seconds, at 50° C. for 5 seconds and at 60° C. for 4 minutes was conducted 40 times. After the reaction, the reaction mixture was transferred into a 1.5 mL Eppendorf tube, and 3M sodium acetate (1 µL), 99.5% ethanol (25 µL) and 125 mM EDTA solution (1 µL) were added thereto. The Eppendorf tube was flipped for mixing the mixture well, and then the mixture was left still at room temperature for 15 minutes. After centrifugation at 14,000 rpm, 4° C. for 20 minutes, the supernatant was removed carefully using a yellow tip, and 70% ethanol (35 µL) was added thereto to be mixed well. Again, after centrifugation at 14,000 rpm, 4° C. for 10 minutes, the supernatant was completely removed using a yellow tip, and the precipitate was left still at room temperature for 10 minutes with the lid open for drying.

To the dried pellet, formamide (manufactured by Applied Biosystems, 10 µL) was added, and the mixture was analyzed by using an ABI PRISM (registered trademark) 3100-Avant Genetic Analyzer (manufactured by Applied Biosystems) in a gene experiment facility, General Research Center, Kochi University. The nucleotide sequence of an expression clone plasmid vector was prepared by preliminarily incorporating nucleotide sequences of a promoter, an antibiotic resistance gene and a terminator into a nucleotide sequence of a destination plasmid using gene analysis software Vector NTI Advance Ver 10.0 (manufactured by Invitrogen). Next, the nucleotide sequence of the expression clone plasmid vector prepared on the computer was compared with the nucleotide sequence of the expression clone plasmid vector experimentally determined according to the above method by alignment using AlignX of Vector NTI Advance Ver 10.0, to confirm that the intended gene was introduced into the expression clone plasmid vector prepared in Example 2(3).

Figure 1:
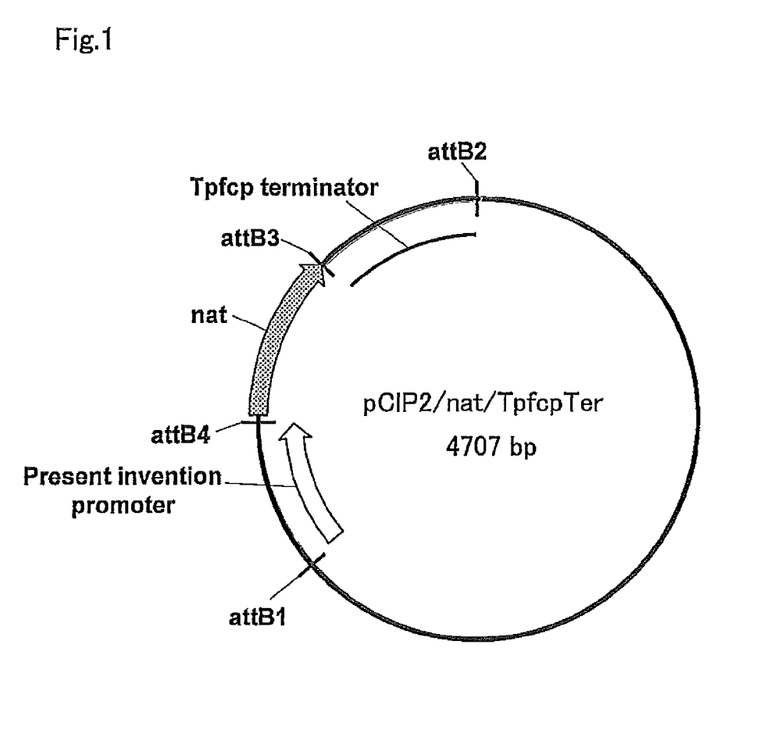
FIG. 1 demonstrates one example of a structure of a plasmid vector containing a promoter according to the present invention.
Figure 2:
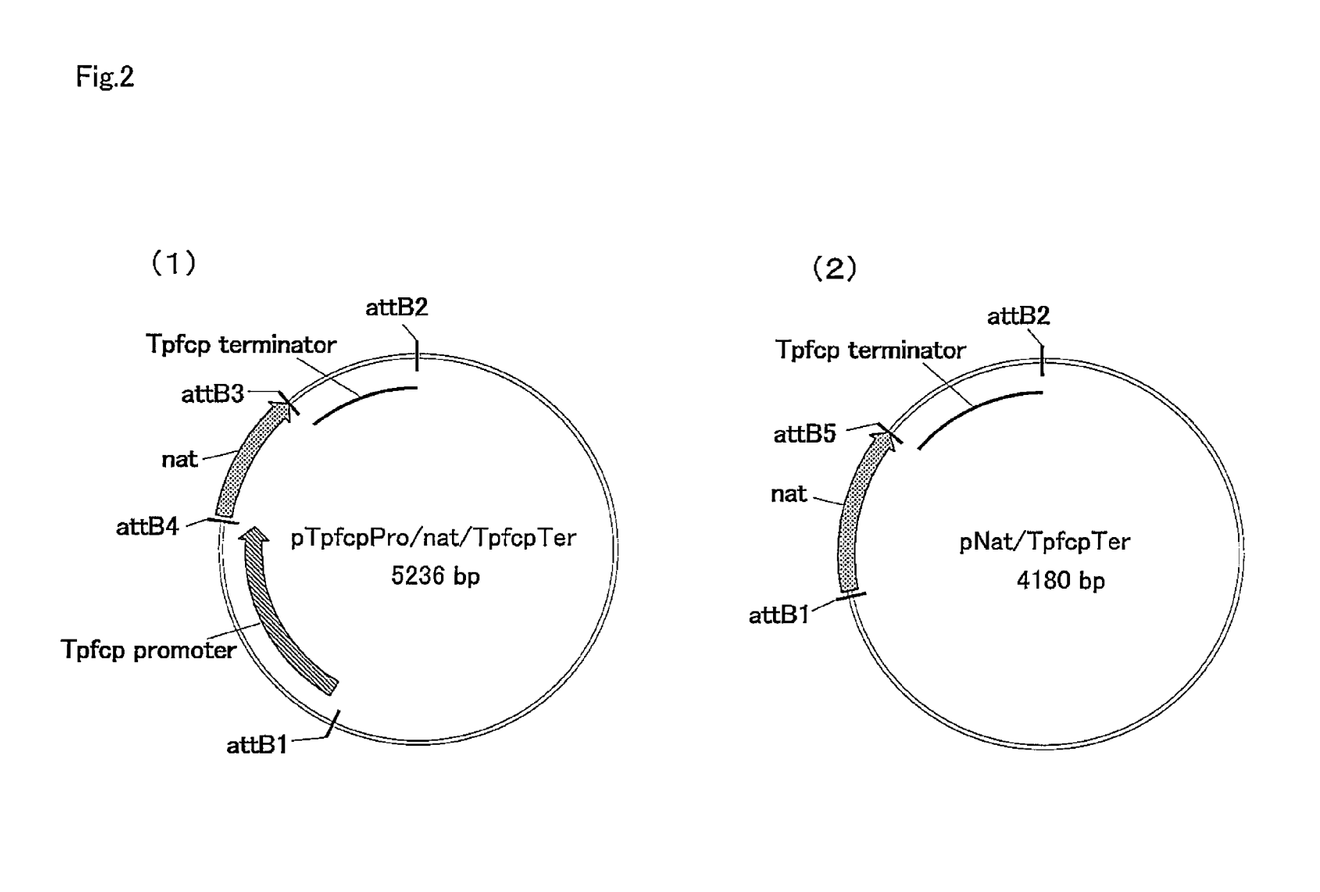
FIG. 2 demonstrates structures of control plasmid vectors to be compared with the present invention promoter.

The structure of the obtained expression clone plasmid vector is shown in FIG. 1.

In addition, plasmids were prepared as controls in a similar manner. One of the plasmids was pTpfcpPro/nat/TpfcpTer, which was similar to the above-described plasmid except that the promoter of ClorDNA virus was replaced with an fcp promoter of centric diatom *Thalassiosira pseudonana*. Another plasmid was pNat/TpfcpTer, which corresponded to the above-described plasmid without promoter. The structures thereof are respectively shown as FIGS. 2(1) and 2(2).

Example 3

Transformation of Centric Diatom

A centric diatom *Chaetoceros* sp. was transformed using the three plasmid vectors prepared in Example 2.

Specifically, the plasmid vectors which had both of an antibiotic resistance gene and an fcp terminator of *Thalassiosira pseudonana* and which had either of a promoter of ClorDNA virus (ClorDNAV) or an fcp promoter of *Thalassiosira pseudonana* was adhered to a tungsten particle M17 having an average particle diameter of 1.1 µm. In addition, the plasmid vector without promoter was also adhered to the particle. Separately, centric diatom *Chaetoceros* sp. was spread on a solid-phase medium in an amount of $1 \times 10^8$ cells per one plate. The tungsten particle was hit into a cell at a He gas pressure of 1350 psi by laminating two rupture disks 650 psi (manufactured by Bio-Rad) and using a particle gun (manufactured by Bio-Rad, Biolistic PDS-1000/He Particle Delivery System). Then, the cell was cultured in a 0.3% agarose HGS (high-intensity agarose, manufactured by Wako Pure Chemical Industries) f/2 medium containing 500 µg/mL Nourseothricin, and the number of the colonies per $1 \times 10^8$ cells was measured. The result is shown in Table 1.

TABLE 1

| Promoter | The number of transformed cells (colonies/$10^8$ cells) |
|---|---|
| ClorDNAV Promoter of the present invention | 13 |
| fcp promoter of *T. pseudonana* | 1 |
| None | 0 |

Transformation of the colony of the cell grown in the medium containing antibiotic was confirmed by PCR. The colony of the grown cell was cultured in a 100 mL medium, and algal cells were collected. Then, genomic DNA was extracted using DNA Extraction Kit (DNeasy (registered trademark) Plant Mini Kit manufactured by Qiagen). PCR was carried out using the obtained genomic DNA as a template and the primer (SEQ ID NO:5) specific for the C1P2 promoter, the primer (SEQ ID NO:6) specific for the incorporated antibiotic gene (nat) and Mighty Amp (registered trademark) DNA Polymerase (manufactured by TAKARA). The condition of PCR was basically similar to Example 1(2), and the cycle number was 30 and the annealing temperature was 55° C. An electrophoretic image analyzing the obtained amplified DNA is shown in FIG. 3.

Figure 3:
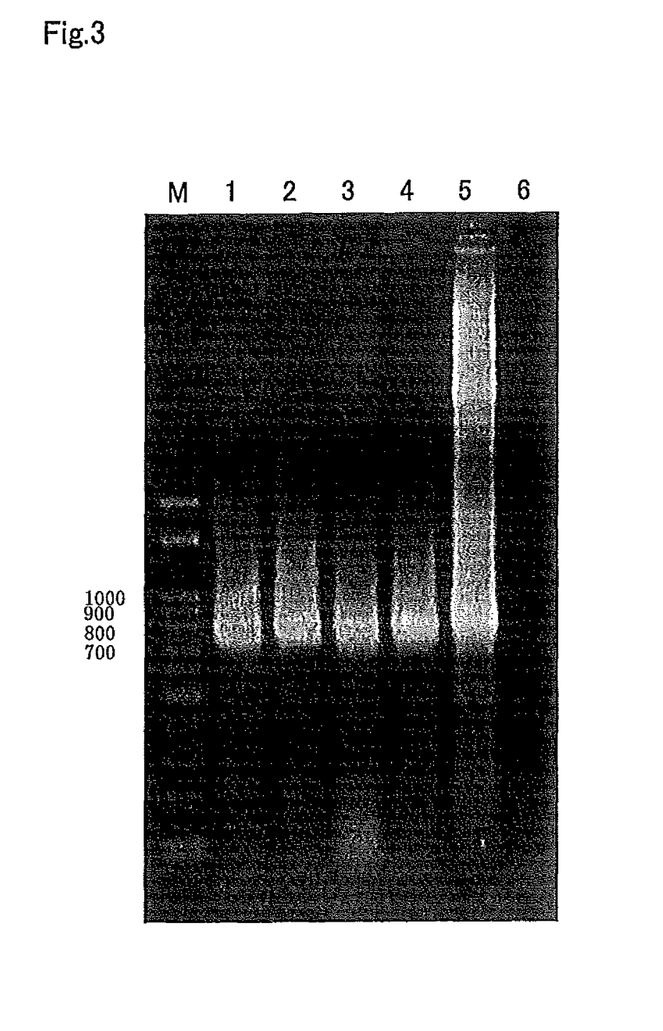
FIG. 3 is an electrophoresis photograph showing a result of an experiment for examining presence of an introduced gene contained in an algal cell transformed by the present invention method.

In FIG. 3, "M" is a molecular weight marker, "1 to 4" are lanes of strains transformed with a plasmid vector containing a promoter according to the present invention and an antibiotic gene (nat), "5" is a lane of positive control using a plasmid vector containing the promoter according to the present invention and an antibiotic gene (nat), and "6" is a lane of negative control using wild Chaetoceros sp. strain.

Discussion of Experimental Result (1) Transforming Ability

As evidenced by the result of Example 3, when a promoter was not introduced into a vector, a transfectant could not obtained, and when a conventional virus promoter was used, only a little amount of transfectant could be obtained.

On the contrary, when the promoter according to the present invention was used, more than 10 times amount of transfectant could be obtained. Therefore, marine algae can be transformed with high efficiency by using the promoter according to the present invention.

(2) Nucleotide Sequence of the Promoter According to the Present Invention

In general, there are a core promoter region to which a transcription binding factor for starting transcription binds and a gene transcription regulating region located upstream of the core promoter region in a promoter region of eukaryote. Also in a viral promoter, it is known that there are motif sequences often found in a core promoter region of eukaryote, such as a TATA box (5'-TATAWAW-3' (wherein W represents A or T)) and an initiator element (Inr). In light of the fact, a nucleotide sequence of the promoter of SEQ ID NO: 1 according to the present invention was analyzed by using PLACE Signal Scan Search and compared.

As a result, in the promoter of SEQ ID NO:1 according to the present invention, a TATA box (285 to 289 in SEQ ID NO:1), a ACGTA box (337 to 341 in SEQ ID NO:1) and 5'-TCAT$_{+1}$AAA-3' (457 to 463 in SEQ ID NO:1) which is considered to be an initiator element of algae were found. The initiator element is somewhat different from the Inr sequences of the other organisms, for example, 5'-YYA$_{+1}$NWYY-3' of mammal (wherein W is A or T, Y is C or T. The same shall apply hereinafter.) (Javahery, R. et al., Molecular and Cellular Biology, 14, pp. 116-127 (1994)), 5'-YCA$_{+1}$TTYY-3' of oomycota (Mcleod, A et al., Eukaryotic Cell, 3, pp. 91-99 (2004)), 5'-TCA$_{+1}$KTY-3' of drosophila (wherein K is G or T.) (Purnell, B. A. et al., Genes & Development, 8, pp. 830-842 (1994)) and 5'-TCA$_{+1}$YW-3' of trichomonad (Liston, D. R. et al., Molecular and Cellular Biology, 19, pp. 2380-2388 (1999)).

In addition to the above result, the present inventors found that the promoter which includes the above Inr and which is derived from CsetDNA virus does not act on centric diatom. The CsetDNA virus is closely related to ClorDNA virus used in the present invention. Therefore, it can be considered that the reason why the polynucleotide (1) according to the present invention can show high transformation ability is that undiscovered sequence other than initiator element serves as core element.

Hereinafter, further experiments are described.

Example 4

Identification of Important Part of the Promoter (1) Isolation of ClorDNA Virus Promoter Three sequences which existed in the upstream sequence of ORF of a structural protein and of which lengths were different from each other were prepared similarly to Example 1(2) except that the primers were changed to the ones shown in Table 2 in the PCR. The annealing parts shown in Table 2 represent the base number in SEQ ID NO:7, which is upstream sequence of the ORF sequence.

TABLE 2

| Primer name | Sequence No. | Annealing part |
|---|---|---|
| CIP2L/attB1 | 2 | 9-25 |
| CIP2L/2/attB1 | 8 | 281-298 |
| CIP2L/5/attB1 | 9 | 424-440 |
| CIP2R/2/attB4 | 10 | 490-507 |

Specifically, ClorDNA virus promoter DNAs of which lengths were different each other were obtained using CIP2R/2/attB4 as a 3' primer and either of $1^{st}$ to $3^{rd}$ primers in Table 2 as 5' primers. Hereinafter, the obtained DNAs are referred to as Promoters 1, 2 and 3 in order of the length.

(2) Preparation of Plasmid Vector

Plasmid vectors into which the ClorDNA virus promoter DNAs obtained in the above (1) were introduced were produced similarly to Example 2. In addition, the vectors which respectively have an endogenous promoter of centric diatom Thalassiosira pseudonana or no promoter were similarly prepared for comparison.

(3) Transformation Experiment

Centric diatom Chaetoceros sp. was transformed using the plasmid vectors prepared in the above (2) similarly to Example 3, and the number of the colonies per the total cell number "$5 \times 10^8$" were measured. Each experiment was repeated three times. The results are shown in Table 3.

TABLE 3

| Promoter | Number of transformed colonies |
|---|---|
| 1 | 8.35 ± 4.59 |
| 2 | 5.00 ± 4.10 |
| 3 | 0 |
| Endogenous promoter | 8.35 ± 4.59 |
| none | 0 |

As the result demonstrated in Table 3, among the ClorDNA virus promoter DNAs prepared in the above (1), when promoter 2 (SEQ ID NO:12; which corresponded to $281^{st}$ to $507^{th}$ base sequence in SEQ ID NO:7) having a moderate length was used, centric diatom was sufficiently transformed with high efficiency. On the other hand, when the shortest Promoter 3, which corresponded to $424^{th}$ to $507^{th}$ base sequence in SEQ ID NO:7 and $144^{th}$ to $230^{th}$ base sequence in SEQ ID NO:12, was used, centric diatom was not transformed at all. Therefore, it can be considered that there is an important sequence for transforming algae in the $1^{st}$ to $143^{rd}$ base sequence of SEQ ID NO:12 (SEQ ID NO:13).

In addition, when longer Promoter 1 (SEQ ID NO:11; which corresponded to 9th to 507th base sequence in SEQ ID NO:7) was used, centric diatom was transformed with higher efficiency. Therefore, it can be considered that there is a sequence which plays a peripheral role for transforming algae in the 9th to 280th base sequence of SEQ ID NO:7.

As described above, the following facts were clarified:
1) there is a very important sequence for transforming algae in the promoter of SEQ ID NO:13;
2) the promoter of SEQ ID NO:12 is very useful for transforming algae; and
3) the promoter of SEQ ID NO:11 has more effective transformation ability.

Example 5

Identification of Important Part of the Promoter

Pennate diatom in addition to centric diatom were transformed using the plasmid vector into which the promoter of SEQ ID NO:12 was introduced. Specifically, the diatoms shown in Table 4 were transformed similarly to Example 3, and the number of colonies per the number of cell ($1 \times 10^8$ in total) was measured. Each experiment was repeated three times. In addition, a similar experiment except for using a plasmid vector without a promoter as a negative control was carried out. The results are shown in Table 4.

TABLE 4

| Diatom | | | Number of |
|---|---|---|---|
| Species | Strain | Promoter | transformed colonies |
| Centric diatom | | | |
| Chaetoceros neogracile | | 1 | 5.00 ± 8.66 |
| | | none | 0 |
| Pennate diatom | | | |
| Phaeodactylum tricornutum | UTEX 646 | 1 | 2.00 ± 1.73 |
| | | none | 0 |

Algae are mainly classified into Pennate diatom and centric diatom, and the specificity of conventional promoters for the species are high. On the other hand, as the result of Table 4, it was demonstrated that the promoter according to the present invention has low specificity and can be widely used for efficiently transforming various algae.

The invention claimed is:

1. A vector comprising a promoter sequence,
wherein the vector comprises a polynucleotide sequence comprising the promoter sequence, and wherein the polynucleotide sequence is selected from the group consisting of SEQ ID NO: 1, SEQ ID NO: 11, SEQ ID NO: 12, and SEQ ID NO: 13.

2. The vector of claim 1, wherein the vector comprises SEQ ID NO: 1.

3. The vector of claim 1, wherein the vector comprises SEQ ID NO: 11.

4. The vector of claim 1, wherein the vector comprises SEQ ID NO: 12.

5. The vector of claim 1, wherein the vector comprises SEQ ID NO: 13.

6. The vector of claim 1, wherein the vector further comprises a gene encoding an arbitrary protein.

7. The vector of claim 6, wherein the promoter sequence is operably linked to the gene.

8. A method for transforming an alga, comprising the steps of
producing the vector of claim 7; and
introducing the vector into the algal cell.

9. The vector of claim 7, wherein the vector comprises SEQ ID NO: 1.

10. The vector of claim 7, wherein the vector comprises SEQ ID NO: 11.

11. The vector of claim 7, wherein the vector comprises SEQ ID NO: 12.

12. The vector of claim 7, wherein the vector comprises SEQ ID NO: 13.

13. A method for transforming an alga, comprising the steps of
producing the vector of claim 9; and
introducing the vector into the algal cell.

14. A method for transforming an alga, comprising the steps of
producing vector of claim 10; and
introducing the vector into the algal cell.

15. A method for transforming an alga, comprising the steps of
producing the vector of claim 11; and
introducing the vector into the algal cell.

16. A method for transforming an alga, comprising the steps of
producing the vector of claim 12; and
introducing the vector into the algal cell.

* * * * *